United States Patent
Thinon et al.

(10) Patent No.: US 11,866,396 B2
(45) Date of Patent: *Jan. 9, 2024

(54) APPARATUS AND PROCESS FOR PRODUCING LIGHT OLEFINS AND AROMATICS BY CATALYTIC CRACKING

(71) Applicant: IFP Energies nouvelles, Rueil-Malmaison (FR)

(72) Inventors: Olivier Thinon, Rueil-Malmaison (FR); Anne Claire, Rueil-Malmaison (FR); Vania Santos-Moreau, Rueil-Malmaison (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/122,239

(22) Filed: Dec. 15, 2020

(65) Prior Publication Data
US 2021/0179515 A1 Jun. 17, 2021

(30) Foreign Application Priority Data
Dec. 16, 2019 (FR) .................... 19/14.507

(51) Int. Cl.
| | | |
|---|---|---|
| *C07C 4/06* | (2006.01) | |
| *C07C 4/04* | (2006.01) | |
| *C07C 5/03* | (2006.01) | |
| *B01J 8/22* | (2006.01) | |
| *B01J 8/24* | (2006.01) | |

(52) U.S. Cl.
CPC .............. *C07C 4/06* (2013.01); *B01J 8/22* (2013.01); *B01J 8/24* (2013.01); *C07C 4/04* (2013.01); *C07C 5/03* (2013.01)

(58) Field of Classification Search
None
See application file for complete search history.

(56) References Cited

U.S. PATENT DOCUMENTS

| | | | | | |
|---|---|---|---|---|---|
| 3,281,351 A | * | 10/1966 | Macqueen | ........... | C10G 70/042 585/804 |
| 3,406,217 A | * | 10/1968 | Davison | ................. | C10G 69/06 208/92 |
| 3,472,909 A | * | 10/1969 | Raymond | .............. | C10G 69/06 208/89 |
| 3,537,982 A | * | 11/1970 | Burich | ................... | C10G 45/32 208/143 |

(Continued)

FOREIGN PATENT DOCUMENTS

WO 16098909 A1 6/2016

OTHER PUBLICATIONS

Search report in corresponding FR 1914507 dated Aug. 20, 2020 (pp. 1-9).

*Primary Examiner* — Tam M Nguyen
(74) *Attorney, Agent, or Firm* — Millen, White, Zelano & Branigan, P.C.; Csaba Henter

(57) ABSTRACT

The present invention relates to an NCC process and an apparatus for producing light olefins and aromatics, wherein the C5+ fraction (16) of the cracking effluent is separated into a C5 fraction (25) recycled into the NCC reactor (4) and a C6+ fraction (26), and wherein the C6+ fraction (26) is sent into an aromatics extraction unit (30) to produce an aromatics-enriched fraction (31) and a low-aromatics fraction (32).

15 Claims, 1 Drawing Sheet

(56) References Cited

U.S. PATENT DOCUMENTS

| | | | | |
|---|---|---|---|---|
| 3,702,292 | A | * | 11/1972 | Burich ................... C10G 69/10 422/139 |
| 3,827,969 | A | * | 8/1974 | Wilson et al. ......... C10G 69/06 208/89 |
| 7,666,299 | B2 | * | 2/2010 | Wu .......................... C10G 7/08 208/321 |
| 2007/0083071 | A1 | | 4/2007 | Choi et al. |
| 2013/0261364 | A1 | * | 10/2013 | Ercan ....................... B01J 29/44 585/475 |
| 2016/0369190 | A1 | * | 12/2016 | Ward .................... C10G 69/06 |
| 2017/0009156 | A1 | * | 1/2017 | Pelaez ................... C10G 69/04 |
| 2017/0058210 | A1 | * | 3/2017 | Pelaez ................... C10G 57/00 |
| 2018/0155633 | A1 | * | 6/2018 | Al-Ghamdi ............ C10G 9/005 |
| 2018/0163147 | A1 | | 6/2018 | Xie et al. |
| 2018/0179453 | A1 | * | 6/2018 | Buchbinder ........... C10G 47/04 |
| 2021/0179514 | A1 | * | 6/2021 | Thinon .................... C07C 4/04 |

\* cited by examiner

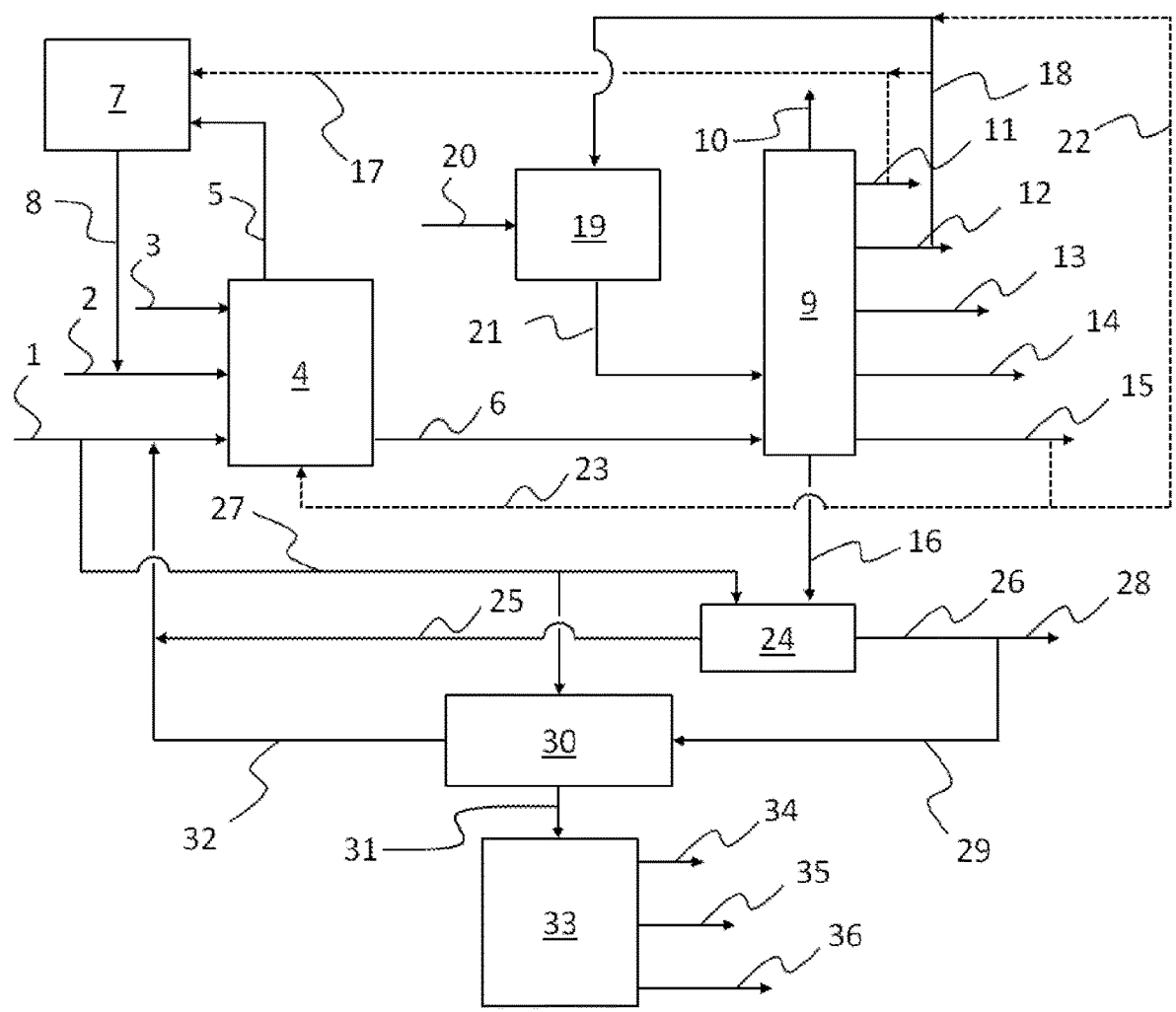

APPARATUS AND PROCESS FOR PRODUCING LIGHT OLEFINS AND AROMATICS BY CATALYTIC CRACKING

TECHNICAL FIELD

The present invention relates to an apparatus and a process which are commonly referred to as NCC (naphtha catalytic cracking) for producing light (C2-C4) olefins, and more particularly ethylene, propylene and aromatics, from a feedstock of hydrocarbons, primarily naphthas and petroleums, by catalytic conversion. The need for low-emission fuels has created increased demand for light olefins for use in processes of alkylation, oligomerization, and synthesis of methyl tert-butyl ether (MTBE) and ethyl tert-butyl ether (ETBE). Furthermore, the demand for light olefins, especially ethylene and propylene, at low cost continues to be studied to act as a raw material for the production of polyolefins, especially polyethylene and polypropylene. There is also great demand for the production of aromatics and in particular BTX (Benzene, Toluene and Xylene) at low cost.

PRIOR ART

Steam cracking, the dehydrogenation of propane, metathesis, MTO (methanol to olefins) or the FCC (fluid catalytic cracking) technology are processes which produce virtually all of the ethylene and propylene that are needed to meet global demand. The hydrocarbons used as raw material for the production of light olefins comprise butane, propane, condensates from natural gas, liquid hydrocarbon fractions from the distillation of petroleum, and carbonaceous materials including coal, recycled plastics or any organic material.

The relatively recent interest in the implementation of an apparatus and a process for producing light olefins by catalytic cracking of naphtha feedstock arises, therefore, from the need to have light olefins for petrochemistry, in addition to the traditional source of naphtha steam cracking, because of:
  the existence of an increasing imbalance between the production of propylene and the production of ethylene, especially with the success of steamcrackers on an ethane feedstock which produces less propylene,
  the anticipated availability of naphtha owing to the reduction in consumption of petrol, the introduction of alternative fuels, and the large-scale market entry of condensates (obtained from shale, for example), and
  the wish to reduce the energy costs of producing olefins, and especially propylene, and the reduction in emissions of $CO_2$ which follow from a lower-temperature operation than naphtha steam cracking, the catalytic activity reducing the need for high temperatures.

The NCC process has been developed for the production of light olefins. It is operated generally in the presence of a catalyst, in the majority of cases a zeolitic catalyst, at a temperature of the order of 600° C., in order to maximise the yield of light olefins and especially of propylene. According to configurations, the NCC process enables a potential increase in the quantity of propylene produced per tonne of naphtha, and in certain cases a greater production of propylene than the steamcracker; to improve exploitation of the naphtha in the form of high added value products for which demand is constantly on the rise, and especially for propylene, ethylene and BTX; and to crack the naphtha at a temperature 150 to 200° C. lower than the temperature used for thermal steam cracking, operating generally at between 800 and 900° C., so as to lower the energy cost of producing propylene and ethylene, while reducing the emissions of $CO_2$.

The steamcracker is one of the main processes currently used to produce light olefins from naphtha and natural gas. This process, being a thermal process operated at high temperatures, produces more ethylene, and, depending on the operating conditions, the mass ethylene/propylene ratio is often of the order of 2. When the feedstocks to be treated are liquid feedstocks with substantial volumes of olefins, there may be operation difficulties, with the formation of substantial amounts of coke. This process also necessitates substantial levels of dilution with steam.

With the increasing interest for the production of light olefins, FCC units have been operated in such a way as to maximize the production of these compounds (see, for example, U.S. Pat. Nos. 4,830,728, 6,489,530A, US2006108261A, CN102746888A). The difficulty of producing light olefins by FCC processes is that it is very difficult to maximize the yield of light olefins while maintaining a high conversion.

Other processes which allow the transformation of gasoline or naphtha-type liquid feedstocks into light olefins, and especially into propylene, have been developed with the objective of enhancing the conversion and the yield of light olefins (see, for example, US2009288985A, US2009143629A, and U.S. Pat. No. 3,776,838A).

SUMMARY OF THE INVENTION

A first object of the present description is to provide a process for enhancing the production of light (C2-C4) olefins and BTX from naphtha.

The present invention enables the yield of light olefins to be maximized, by recycling the C5+ fraction which has undergone an extraction of the aromatics with prior fractionation of the C5+ fraction into C5 and C6+.

According to a first aspect, the present invention relates to a process for producing olefins having a number of carbon atoms of between 2 and 4 and aromatics by catalytic cracking, comprising the following steps:
  contacting some or all of a feedstock comprising naphtha, a catalyst and a diluent in a naphtha catalytic cracking reactor to convert at least partly the naphtha-comprising feedstock into olefins having a number of carbon atoms of between 2 and 4 and to produce a cracking effluent;
  sending the cracking effluent into a first separating section to produce at least the following fractions:
    a fraction comprising ethylene,
    a fraction comprising propylene, and
    a fraction comprising compounds comprising at least 5 carbon atoms, comprising paraffins, olefins and aromatics;
  sending at least part of the fraction comprising compounds comprising at least 5 carbon atoms into a second separating section to produce the following fractions:
    a fraction comprising compounds comprising 5 carbon atoms, and
    a fraction comprising compounds comprising at least 6 carbon atoms which is rich in aromatics;
  sending at least part of the fraction comprising compounds comprising at least 6 carbon atoms into an aromatics extraction unit to produce the following fractions:

an aromatics-enriched fraction, and
a low-aromatics fraction; and
recycling at least partly the fraction comprising compounds comprising 5 carbon atoms into the naphtha catalytic cracking reactor.

According to one or more embodiments, the process further comprises the following step:
sending at least part of the aromatics-enriched fraction (31) into an aromatics separation unit (33) to produce at least the following fractions:
a benzene-rich fraction (34),
a toluene-rich fraction (35), and
at least one xylenes-rich fraction (36).

According to one or more embodiments, the low-aromatics fraction is recycled at least partly into the naphtha catalytic cracking reactor.

According to one or more embodiments, the first separating section further produces at least one of the following fractions:
a fraction comprising hydrogen,
a fraction comprising methane,
a fraction comprising ethane and/or propane, and
a fraction comprising compounds comprising 4 carbon atoms.

According to one or more embodiments, the naphtha catalytic cracking reactor (4) is operated as a turbulent fluidized bed.

According to one or more embodiments, the first separating section further produces a fraction comprising ethane and/or propane, and the fraction comprising ethane and/or propane is at least partly sent into a steam cracking furnace fed with steam to produce a steam cracking effluent comprising ethylene and/or propylene.

According to one or more embodiments, the fraction comprising ethane and/or propane is admixed with the steam in a mass [steam]/[fraction comprising ethane and/or propane] ratio of between 0.2 and 0.8, and undergoes cracking at a temperature of between 750 and 900° C. in the steam cracking furnace.

According to one or more embodiments, the steam cracking effluent is sent to the first separating section.

According to one or more embodiments, the first separating section produces at least one fraction comprising compounds comprising 4 carbon atoms, and at least a part of the fraction comprising compounds comprising 4 carbon atoms is recycled to the steam cracking furnace.

According to one or more embodiments, the first separating section produces at least one fraction comprising compounds comprising 4 carbon atoms, and at least part of the fraction comprising compounds comprising 4 carbon atoms is recycled to the naphtha catalytic cracking reactor.

According to one or more embodiments, the naphtha-comprising feedstock comprises aromatics, and some or all of the naphtha-comprising feedstock is sent into the second separating section or into the aromatics extraction unit.

According to one or more embodiments, a coked catalyst is withdrawn from the naphtha catalytic cracking reactor, is separated from the cracking effluent, is stripped and is regenerated in a regenerator to produce a regenerated catalyst which is recycled into the naphtha catalytic cracking reactor.

According to one or more embodiments, the first separating section produces at least one fraction comprising methane, and the fraction comprising methane is at least partly used as fuel gas feeding the regenerator.

According to one or more embodiments, the first separating section further produces at least one fraction comprising ethane and/or propane, and the fraction comprising ethane and/or propane is at least partly used as fuel gas feeding the regenerator.

According to one or more embodiments, the catalyst comprises at least one zeolite, and the naphtha catalytic cracking reactor is utilized under the following operating conditions: a temperature of between 500 and 700° C.; an absolute total pressure of between 0.1 and 0.5 MPa; a contact time between the naphtha-comprising feedstock and the catalyst of between 200 milliseconds and 20 seconds; and a partial pressure of hydrocarbons in the naphtha-comprising feedstock of between 0.02 and 0.3 MPa.

According to one or more embodiments, the aromatics extraction unit comprises an olefin hydrogenation section for producing a low-olefin hydrogenation effluent comprising paraffins and aromatics; and an extraction section for separating the hydrogenation effluent and producing the aromatics-enriched fraction and the low-aromatics fraction.

According to a second aspect, the present invention relates to an apparatus for producing olefins having a number of carbon atoms of between 2 and 4 and aromatics by catalytic cracking, comprising the following units:
a naphtha catalytic cracking reactor suitable for contacting some or all of a feedstock comprising naphtha, a catalyst and a diluent, converting at least partly the naphtha-comprising feedstock into olefins having a number of carbon atoms of between 2 and 4, and producing a cracking effluent;
a first separating section suitable for treating the cracking effluent and producing at least the following fractions:
a fraction comprising ethylene,
a fraction comprising propylene, and
a fraction comprising compounds comprising at least 5 carbon atoms, comprising paraffins, olefins and aromatics;
a second separating section suitable for treating at least part of the fraction comprising compounds comprising at least 5 carbon atoms, and producing the following fractions:
a fraction comprising compounds comprising 5 carbon atoms, and
a fraction comprising compounds comprising at least 6 carbon atoms which is rich in aromatics;
an aromatics extraction unit suitable for treating at least part of the fraction comprising compounds comprising at least 6 carbon atoms, and producing the following fractions:
an aromatics-enriched fraction, and
a low-aromatics fraction; and
a duct suitable for recycling at least partly the fraction comprising compounds comprising 5 carbon atoms into the naphtha catalytic cracking reactor.

Other features and advantages of the invention of the aforementioned aspects will become apparent on reading the following description of non-limiting exemplary embodiments, with reference to the appended FIGURE described below.

BRIEF DESCRIPTION OF THE DRAWINGS

FIG. 1 shows a scheme of an NCC process according to the present invention for producing light olefins and BTX from naphtha.

DETAILED DESCRIPTION OF THE INVENTION

Embodiments according to the aforementioned aspects will now be described in detail. In the detailed description below, numerous specific details are set out in order to convey a deeper understanding of the apparatus. However, it will be apparent to the skilled person that the device can be implemented without these specific details. In other cases, well-known features have not been described in detail in order to avoid unnecessarily complicating the description.

The invention concerns an NCC process and an apparatus for producing light olefins and BTX, starting from naphtha feedstocks. One advantage of the present invention is that of providing an NCC process and an apparatus which enable substantial yields of light olefins and especially propylene and ethylene, relative to the catalytic cracking processes and apparatuses, and also enable the production of BTX.

Throughout the remainder of the text, light olefins are understood to be olefins having a number of carbon atoms of between 2 and 4. The light olefins produced by the process according to the invention are preferably ethylene and propylene.

Feedstock

According to the invention, the feedstock used is a feedstock comprising naphtha. According to one or more embodiments, the feedstock consists essentially of naphtha. For example, the feedstock may comprise at least 90 weight %, preferably at least 95 weight %, very preferably at least 99 weight % of naphtha.

According to one or more embodiments, the naphtha is a gasoline feedstock comprising and preferably consisting of hydrocarbon compounds having 4 to 15 carbon atoms, preferably 5 to 14 carbon atoms.

According to one or more embodiments, said gasoline feedstock has an initial boiling point of between 20 and 100° C. and preferably of between 20 and 80° C. and more preferably between 25 and 60° C., and a final boiling point of between 80 and 250° C. and preferably between 100 and 220° C. and more preferably between 100 and 180° C.

According to one or more embodiments, said gasoline feedstock is a light naphtha feedstock with a final boiling point of 80° C. to 100° C. or a heavy naphtha feedstock with an initial point of 80° C. to 100° C. and a final boiling point of 150° C. to 220° C.

According to one or more embodiments, the gasoline feedstock comprises a content of paraffins (normal+iso) of between 20 and 90 weight % and preferably between 30 and 85 weight %, a content of olefins of between 0 and 60 weight % and preferably between 0 and 30 weight %, more preferably between 0 and 15 weight %, a content of naphthenes of between 5 and 70 weight % and preferably between 15 and 50 weight %, a content of aromatics of between 0 and 50 weight % and preferably between 0 and 30 weight %, more preferably between 0 and 15 weight %, the weight percentages being expressed relative to the total mass of said feedstock, and the sum of the various components being equal to 100%.

According to one or more embodiments, the gasoline feedstock used in the process according to the invention is paraffinic, meaning that it is made up primarily of iso- and n-paraffins. Said feedstock more preferably comprises paraffins having 4 to 11 carbon atoms and preferably 5 to 9 carbon atoms.

A paraffinic feedstock is understood to be a gasoline feedstock comprising a content of paraffins (normal+iso) of at least 50 weight %, such as of between 50 and 90 weight %, relative to the total mass of said feedstock. According to one or more embodiments, the feedstock comprises at least 60 weight %, preferably at least 70 weight %, very preferably at least 80 weight % of paraffins.

According to one or more embodiments, the gasoline feedstock comprises less than 20 weight % of olefins (having preferably at least 5 and/or at least 9 carbon atoms), preferably less than 17 weight % of olefins and more preferably less than 15 weight % of olefins.

According to one or more embodiments, said gasoline feedstock has come from the direct distillation of petroleum, in which case the feedstock is a straight-run naphtha, and/or has come from one or more gasoline production processes (such as, for example, the fluidized bed catalytic cracking or FCC process, coking or delayed coker or flexicoker process; the hydrocracking process), and/or from a process purge such as isomerization processes. This feedstock is commonly referred to as "Naphtha".

Said gasoline feedstock may optionally undergo a hydrotreating pretreatment step prior to its use in the apparatus and the process according to the invention, so as to limit or eliminate the nitrogen-containing and sulfur-containing impurities and the oxygen-containing derivatives, for example.

According to one or more embodiments, said gasoline feedstock may have come from a Fischer-Tropsch process, before or after hydrotreating and/or hydro-isomerization steps.

Naphtha Catalytic Cracking Step

With reference to FIG. 1, the process according to the present invention comprises an NCC step of producing light olefins by catalytic cracking of a naphtha, in which the feedstock 1 is contacted with a catalyst 2 and a diluent 3 in an NCC reactor 4.

According to one or more embodiments, the operating conditions of the NCC step are as follows: a temperature of between 500 and 700° C., preferably between 550 and 700° C., more preferably still between 580 and 685° C.; an absolute total pressure of between 0.1 and 0.5 MPa and preferably between 0.1 and 0.4 MPa and more preferably between 0.1 and 0.3 MPa; a contact time between the feedstock 1 and the catalyst 2 of between 200 milliseconds (ms) and 20 seconds, preferably between 400 milliseconds and 15 seconds and more preferably between 600 milliseconds and 10 seconds; and a PPHfeed (partial pressure of hydrocarbons in the feedstock) of between 0.02 and 0.3 MPa, preferably between 0.03 and 0.2 MPa and more preferably between 0.04 and 0.15 MPa.

According to one or more embodiments, the feedstock 1 is contacted with the catalyst 2 in a reactor operating as a fixed bed, a moving bed or a fluidized bed, preferably in a reactor operating as a fluidized bed, very preferably as a turbulent fluidized bed. In the present specification, the term "turbulent fluidized bed" signifies a fluidized gas-solid bed in which the volume fraction of solid (particles of catalyst) is between 0.2 and 0.5, preferably between 0.25 and 0.4.

According to one or more embodiments, the diluent 3 is selected from an inert gas such as nitrogen and/or steam. According to one or more embodiments, the diluent 3 is steam. According to one or more embodiments, the diluent 3 is nitrogen. According to one or more embodiments, the amount of diluent 3 is selected to give the abovementioned PPHfeed and the diluent 3 is introduced in an amount representing 0.1 to 40 weight %, preferably 1 to 35 weight % and more preferably of between 1 and 30 weight % relative to the mass of the feedstock 1. According to one or more embodiments, the feedstock 1 is introduced into the NCC reactor 4 as a mixture with steam. The presence of steam enables a lowering of the partial pressure of the feedstock 1, which is thermodynamically unfavourable to the cracking reactions, and an improvement in the fluidization and the thermal transfers. Moreover, the presence of water also makes it possible to limit the hydrogen transfer reactions which lead to the formation of unwanted light alkanes such as methane, ethane and propane.

In the NCC reactor 4, the feedstock 1 is converted by catalytic cracking in the presence of the catalyst 2 into light olefins and especially into ethylene and into propylene, and into BTX (Benzene, Toluene and Xylene).

According to one or more embodiments, at the end of the NCC step, a coked catalyst 5 emerges from the NCC reactor 4 and is advantageously separated from the cracking effluent 6, referred to as NCC effluent, produced during the NCC step, and is stripped and regenerated in a regenerator 7 to produce a regenerated catalyst 8, which is recycled to the NCC reactor 4. Since the catalyst is generally coked, it may be regenerated by burning the coke in the regenerator 7 in contact with combustion air that feeds said regenerator. According to the production of coke in the NCC reactor 4, an external fuel feed may advantageously be injected into the regenerator in order to complete the thermal balance of the process.

The NCC effluent 6 comprises a gaseous fraction containing substantial concentrations of light (C2-C4) olefins and especially of ethylene (C2) and propylene (C3), and a C5+ fraction which, depending on the conditions selected, may contain substantial quantities of BTX.

Specifically, the NCC effluent 6 obtained comprises a mixture of hydrogen, methane, ethane, ethylene, propane, propylene, a C4 fraction comprising butanes and butenes, and a C5+ fraction which contains, in particular, aromatics, such as BTX. The NCC effluent 6 is then advantageously cooled and separated to give the light olefins and, preferably, ethylene and propylene.

Catalyst for the NCC Step

The catalyst 2 may be any type of catalyst for catalytic cracking, preferably containing at least one zeolite, such as a zeolite selected from zeolites NU-86, ZSM-5, ZSM-11, beta, Y, ferrierite, ZSM-22, ZSM-23 and EU-1, alone or in a mixture, preferably from zeolites NU-86, ZSM-5, ZSM-11, beta, Y and ferrierite, alone or a mixture, and very preferably from zeolites Y, NU-86 and ZSM-5, alone or in a mixture.

According to one or more embodiments, the catalyst 2 comprises at least one binder selected from alumina, silica, silica-alumina, magnesia, titanium oxide, zirconia, clays and boron oxide, alone or in a mixture, and preferably from silica, silica-alumina and clays, alone or in a mixture.

According to one or more embodiments, the catalyst 2 comprises, as percentages by mass:

from 20 to 80 weight % of at least one binder;
from 20 to 80 weight % of at least one zeolite selected from zeolites Nu-86, ZSM-5, ZSM-11, beta, Y, ferrierite, ZSM-22, ZSM-23 and EU-1, alone or in a mixture; and
from 0 to 12 weight % of at least one doping element, the percentages being expressed relative to the total mass of said catalyst 2, and the sum of the amounts of said elements being equal to 100%.

According to one or more embodiments, the at least one doping element is selected from phosphorus, magnesium, sodium, potassium, calcium, iron, boron, manganese, lanthanum, cerium, titanium, tungsten, molybdenum, copper, zirconium and gallium, alone or in a mixture.

NCC Effluent Separation Steps

The NCC effluent 6 is sent to a first separating section 9, in which the NCC effluent 6 is fractionated. According to one or more embodiments, the NCC effluent 6 is (rapidly) quenched, for example by a cooling step, before being fractionated (not shown in the FIGURE). According to one or more embodiments, the first separating section 9 enables separation of the following fractions: hydrogen 10; methane 11; ethane and/or propane 12; ethylene 13; propylene 14; C4 fraction 15 comprising, in particular, butanes and butenes; C5+ fraction 16, comprising paraffins, olefins and aromatics.

According to one or more embodiments, the methane 11, and optionally the ethane and/or the propane, separated in this way, are at least partly used as fuel gas 17, feeding the regenerator 7 in order to complete the thermal balance of the process, since the cracking reactions taking place in the NCC reactor 4 may be highly endothermic.

According to one or more embodiments, the ethane and/or the propane, alone or in a mixture (line 18), are at least partly sent to a steam cracking furnace 19. According to one or more embodiments, the ethane or the propane or the mixture 18 is admixed with steam 20 according to a mass [steam 20]/[fraction comprising ethane and/or propane 12] ratio of between 0.2 and 0.8 and preferably between 0.3 and 0.5, and undergoes cracking at a temperature of between 750 and 900° C. and preferably between 780 and 850° C.

According to one or more embodiments, the steam cracking effluent 21 is enriched in ethylene and/or propylene relative to the ethane and/or propane fraction (12). According to one or more embodiments, the steam cracking effluent 21 comprises an ethylene content of between 30 and 70 weight % and preferably between 35 and 55 weight %, a propylene content of between 5 and 25 weight % and preferably between 5 and 15 weight %, the weight percentages being expressed relative to the total mass of said effluent, and the sum of the various components being equal to 100%. The steam cracking effluent 21 is sent to the first separating section 9, after having been optionally cooled to a temperature of between 500 and 700° C., preferably between 550 and 650° C.

According to one or more embodiments, at least part of the C4 fraction 15 is recycled to the steam cracking furnace 19 (line 22) and/or the NCC reactor 4 (line 23). According to one or more embodiments, at least part of the C4 fraction 15 is separated into an olefinic C4 fraction and a paraffinic C4 fraction, and at least part of the paraffinic C4 fraction is recycled to the steam cracking furnace 19 and/or the NCC reactor 4.

According to one or more embodiments, at least part of the C5+ fraction 16 is sent to a second separating section 24, to produce a C5 fraction 25 (composed primarily of paraffins and olefins) and a C6+ fraction 26 which is enriched in aromatics in relation to the C5+ fraction 16.

According to one or more embodiments, when the feedstock 1 comprises aromatics, for example when the feedstock 1 comprises more than 15 weight % of aromatics, preferably more than 25 weight %, more preferably more than 35 weight %, some or all of the feedstock 1 is advantageously sent (line 27) to the second separating section 24 of the NCC effluent separation step, in a mixture with at least part of the C5+ fraction 16, to produce the C5 fraction 25, which is directly recycled to the NCC reactor 4, and the aromatics-rich C6+ fraction 26. These configurations are of particular interest for highly aromatic feedstocks, since they enable the extraction of the aromatics from the gasoline feedstock before it is sent into the NCC reactor.

According to one or more embodiments, the second separating section 24 comprises or consists of a distillation column. The fraction enriched in C5 fraction 25 is withdrawn at the top of the distillation column. According to one or more embodiments, the C5 fraction 25 comprises between 80 and 100 weight % of the compounds having 5 carbon atoms, preferably between 90 and 99 weight %, and very preferably between 95 and 99 weight %. The C6+ fraction 26 is withdrawn at the column bottom. The C6+ fraction 26 advantageously comprises the majority of the aromatic compounds of the C5+ fraction 16.

According to one or more embodiments, the C5 fraction 25 is at least partly recycled to the NCC reactor 4 so as to increase the yield of light olefins. According to one or more embodiments, the C5 fraction 25 recycled to the NCC reactor 4 contains between 5 and 40 weight %, preferably between 5 and 30 weight %, of olefins. Since the olefins are more reactive in the cracking reactions than the paraffins having the same carbon number, the recycling of the C5 olefin-rich C5 fraction 25 to the NCC reactor 4 is beneficial to increasing the production of light olefins.

The C6+ fraction 26 may advantageously be at least partly removed from the process (line 28).

According to one or more embodiments, at least part of the C6+ fraction 26 is sent (line 29) to an aromatics extraction unit 30 to produce an aromatics-enriched fraction 31, enriched preferably in BTX (benzene, toluene and xylenes), and a low-aromatics fraction 32, preferably a low-BTX fraction. The aromatics extraction unit 30 may be implemented according to various processes known to the skilled person. According to one or more embodiments, the aromatics extraction unit 30 comprises a section for hydrogenating olefins, to produce a low-olefin hydrogenation effluent comprising paraffins and aromatics; and an extraction section for separating the hydrogenation effluent and producing the aromatics-enriched fraction 31 and the low-aromatics fraction 32. Accordingly, in one or more embodiments, the low-aromatics fraction 32 is also depleted in olefins.

According to one or more embodiments, when the feedstock 1 comprises aromatics, for example when the feedstock 1 comprises more than 15 weight % of aromatics, preferably more than 25 weight %, more preferably more than 35 weight %, some or all of the feedstock 1 may advantageously be sent (line 27) directly to the aromatics extraction unit 30 in a mixture with at least part of the C6+ fraction 26, to carry out the extraction of the aromatics, preferably the BTX, from some or all of the feedstock 1. These configurations are of particular interest for highly aromatic feedstocks, since they enable the aromatics to be extracted from the gasoline feedstock before it is sent into the NCC reactor.

According to one or more embodiments, the low-aromatics fraction 32 is at least partly recycled to the NCC reactor 4 so as to increase the yield of olefins.

According to one or more embodiments, at least part of the aromatics-enriched fraction 31 is sent to an aromatics separation unit 33 to produce at least: a benzene-rich fraction 34, a toluene-rich fraction 35, at least one xylenes-rich fraction 36 (fraction of para-xylene, ortho-xylene and/or meta-xylene, and preferably a para-xylene fraction), and optionally at least one fraction of aromatics having at least 9 carbon atoms.

The aromatics separation unit 33 may be implemented according to various processes known to the skilled person. According to one or more embodiments, the aromatics separation unit 33 comprises an apparatus for converting aromatic compounds, referred to as "aromatics complex". Within the aromatics complex, the benzene and alkylaromatics (toluene, xylenes, ethylbenzene and aromatic compounds having 9 or more carbon atoms) are extracted by means of a fractionating train. Furthermore, an aromatics complex generally possesses at least one catalytic unit such as the following:

the isomerization of aromatic compounds having 8 carbon atoms—this unit enables the conversion at least partly of ortho-xylene, meta-xylene and ethylbenzene into para-xylene;

transalkylation, which enables xylenes to be produced from a mixture of toluene (and optionally benzene) and aromatic compounds having 9 or more carbon atoms, such as trimethylbenzenes and tetramethylbenzenes; and disproportionation of toluene, which enables the production of benzene and xylenes.

An aromatics complex generally also possesses a section for separating C8 aromatics by simulated moving bed adsorption to produce an extract (para-xylene and desorbent, such as toluene) and a raffinate (ortho-xylene, meta-xylene and ethylbenzene), or a crystallizing section in which the para-xylene is isolated in the form of crystals from the remainder of the compounds in a mixture comprising aromatic compounds having 8 carbon atoms.

In the present specification, the term "comprise" is synonymous with (signifies the same thing as) "include" and "contain", and is inclusive or open, and does not exclude other elements which are not stated. It is understood that the term "comprise" includes the exclusive and closed term "consist".

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 19/14.507, filed Dec. 16, 2019, are incorporated by reference herein.

EXAMPLES

Test Conditions:
- turbulent fluidized bed reactor;
- temperature: 682.2° C.;
- pressure: 1.05 bar a (0.105 MPa a);
- diluent: nitrogen;
- PPHfeed: 0.64 bar (0.064 MPa);
- contact time: 3774.08 ms;
- ZSM-5 zeolitic catalyst; and
- feedstock: light naphtha having the characteristics described in table 1.

TABLE 1

| Density at 15° C. | g/cm$^3$ | 0.6687 |
|---|---|---|
| Molar mass | g/mol | 81.82 |
| Simulated distillation | | |
| Initial point ASTM 2887 | ° C. | 30.2 |
| Final point ASTM 2887 | ° C. | 111.2 |
| N paraffins | % m/m | 36.1 |
| Iso paraffins | % m/m | 48.5 |
| Naphthenes | % m/m | 12.1 |
| Aromatics | % m/m | 2.8 |
| Olefins | % m/m | 0 |

TABLE 1-continued

| Benzene | % m/m | 1.72 |
| Toluene | % m/m | 1.0244 |

Examples A

Table 2 describes the comparison of the yields obtained from:
1) the first separating section 9 after passage through the NCC reactor 4 without recycling (not compliant with the present invention);
2) the first separating section 9 after passage through the NCC reactor 4 (not compliant with the present invention), with:
  sending of the C5+ fraction 16 directly into the aromatics extraction unit 30 for extraction of the aromatics-enriched fraction 31 and recycling of the low-aromatics fraction 32;
3) the first separating section 9 after passage through the NCC reactor 4 (compliant with the present invention), with:
  sending of the C5+ fraction 16 into the second separating section 24,
  sending of the C5 fraction 25 into the NCC reactor 4, and
  sending of the C6+ fraction 26 into the aromatics extraction unit 30 for extraction of the aromatics-enriched fraction 31 and recycling of the low-aromatics fraction 32; and
4) the first separating section 9 after passage through the NCC reactor 4 (compliant with the present invention), with:
  sending of the C5+ fraction 16 into the second separating section 24,
  sending of the C5 fraction 25 into the NCC reactor 4,
  sending of the C6+ fraction 26 into the aromatics extraction unit 30 for extraction of the aromatics-enriched fraction 31 and recycling of the low-aromatics fraction 32,
  sending of the ethane and the propane 12 into the steam cracking furnace 19, and
  sending of the steam cracking effluent 21 into the first separating section 9.

TABLE 2

| | # | | | |
| Yields | 1 weight % | 2 weight % | 3 weight % | 4 weight % |
| --- | --- | --- | --- | --- |
| Ethylene | 22.2 | 28.0 | 28.6 | 39.3 |
| Propylene | 18.8 | 23.8 | 24.2 | 25.0 |
| Gasoline | 28.7 | 0.0 | 0.0 | 0.0 |
| BTX | 0.0 | 10.1 | 10.1 | 10.4 |
| Total light olefins (C2 and C3) | 41.0 | 51.8 | 52.8 | 64.3 |
| Total light olefins (C2 and C3) + BTX | 41.0 | 61.8 | 62.8 | 74.7 |

Examples B

Table 3 describes the comparison of the yields obtained from:
1) the first separating section 9 after passage through the NCC reactor 4 without recycling (not compliant with the present invention);
5) the first separating section 9 after passage through the NCC reactor 4 (not compliant with the present invention), with:
  sending of the ethane and the propane 12 into the steam cracking furnace 19, and
  sending of the steam cracking effluent 21 into the first separating section 9; and
4) the first separating unit 9 after passage through the NCC reactor 4 (compliant with the present invention), with:
  sending of the C5+ fraction 16 into the second separating section 24,
  sending of the C5 fraction 25 into the NCC reactor 4,
  sending of the C6+ fraction 26 into the aromatics extraction unit 30 for extraction of the aromatics-enriched fraction 31 and recycling of the low-aromatics fraction 32,
  sending of the ethane and the propane 12 into the steam cracking furnace 19, and
  sending of the steam cracking effluent 21 into the first separating section 9.

TABLE 3

| | # | | |
| Yields | 1 weight % | 5 weight % | 4 weight % |
| --- | --- | --- | --- |
| Ethylene | 22.2 | 31.1 | 39.3 |
| Propylene | 18.8 | 19.8 | 25.0 |
| Gasoline | 28.7 | 20.4 | 0.0 |
| BTX | 0.0 | 0.0 | 10.4 |
| Total light olefins (C2 and C3) | 41.0 | 50.9 | 64.3 |
| Total light olefins (C2 and C3) + BTX | 41.0 | 50.9 | 74.7 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for producing olefins having a number of carbon atoms between 2 and 4 and aromatics by catalytic cracking, comprising the following steps:
  contacting some or all of a feedstock comprising naphtha (1), a catalyst (2) and a diluent (3) in a naphtha catalytic cracking reactor (4) to convert at least partly the naphtha-comprising feedstock (1) into olefins having a number of carbon atoms of between 2 and 4 and to produce a cracking effluent (6);
  sending the cracking effluent (6) into a first separating section (9) to produce at least the following fractions:
    a fraction comprising ethylene (13),
    a fraction comprising propylene (14), and
    a fraction comprising compounds comprising at least 5 carbon atoms (16), comprising paraffins, olefins and aromatics;
  sending at least part of the fraction comprising compounds comprising at least 5 carbon atoms (16) into a second separating section (24) to produce the following fractions:
    a fraction comprising compounds comprising 5 carbon atoms (25), which contains less aromatics than fraction (16), and
    a fraction comprising compounds comprising at least 6 carbon atoms (26) which is enriched in aromatics in relation to fraction (16);

sending at least part of the fraction comprising compounds comprising at least 6 carbon atoms (26) into an aromatics extraction unit (30) to produce the following fractions:
an aromatics-enriched fraction (31), and
a low-aromatics fraction (32);
recycling at least partly the fraction comprising compounds comprising 5 carbon atoms (25), which achieves the recycling of less aromatics than if the same amount of fraction (16) would have been recycled, and recycling the low-aromatics fraction (32) into the naphtha catalytic cracking reactor (4), which achieves the recycling of less aromatics than if the same amount of fraction (26) would have been recycled; and
sending at least part of the aromatics-enriched fraction (31) into an aromatics separation unit (33) to produce at least the following fractions:
a benzene-rich fraction (34),
a toluene-rich fraction (35),
at least one xylenes-rich fraction (36), and
at least one fraction of aromatics having at least 9 carbon atoms.

2. The process for producing olefins according to claim 1, wherein the aromatic compounds of the at least one fraction of aromatics having 9 or more carbon atoms are extracted by a fractionating train.

3. The process for producing olefins according to claim 1, wherein the naphtha catalytic cracking reactor (4) is operated as a turbulent fluidized bed.

4. The process for producing olefins according to claim 1, wherein the first separating section (9) further produces a fraction comprising ethane and/or propane (12), and wherein the fraction comprising ethane and/or propane (12) is at least partly sent into a steam cracking furnace (19) fed with steam (20) to produce a steam cracking effluent (21) comprising ethylene and/or propylene.

5. The process for producing olefins according to claim 4, wherein the fraction comprising ethane and/or propane (12) is admixed with the steam (20) in a mass [steam (20)]/[fraction comprising ethane and/or propane (12)] ratio of between 0.2 and 0.8, and undergoes cracking at a temperature between 750 and 900° C. in the steam cracking furnace (19).

6. The process for producing olefins according to claim 4, wherein the steam cracking effluent (21) is sent into the first separating section (9).

7. The process for producing olefins according to claim 4, wherein the first separating section (9) produces at least one fraction comprising compounds comprising 4 carbon atoms (15), and in which at least a part of the fraction comprising compounds comprising 4 carbon atoms (15) is recycled to the steam cracking furnace (19).

8. The process for producing olefins according to claim 1, wherein the first separating section (9) produces at least one fraction comprising compounds comprising 4 carbon atoms (15), and in which at least a part of the fraction comprising compounds comprising 4 carbon atoms (15) is recycled to the naphtha catalytic cracking reactor (4).

9. The process for producing olefins according to claim 1, wherein the naphtha-comprising feedstock (1) comprises aromatics, and wherein some or all of the naphtha-comprising feedstock (1) is sent into the second separating section (24) or into the aromatics extraction unit (30).

10. The process for producing olefins according to claim 1, wherein a coked catalyst (5) is withdrawn from the naphtha catalytic cracking reactor (4), is separated from the cracking effluent (6), is stripped and is regenerated in a regenerator (7) to produce a regenerated catalyst (8) which is recycled into the naphtha catalytic cracking reactor (4).

11. The process for producing olefins according to claim 10, wherein the first separating section (9) produces at least one fraction comprising methane (11), and wherein the methane-comprising fraction (11) is at least partly used as fuel gas (17) feeding the regenerator (7).

12. The process for producing olefins according to claim 10, wherein the first separating section (9) further produces a fraction comprising ethane and/or propane (12), and wherein the fraction comprising ethane and/or propane (12) is at least partly used as fuel gas (17) feeding the regenerator (7).

13. The process for producing olefins according to claim 1, wherein the catalyst (2) comprises at least one zeolite, and wherein the naphtha catalytic cracking reactor (4) is utilized according to the following operating conditions: a temperature between 500 and 700° C.; an absolute total pressure between 0.1 and 0.5 MPa; a contact time between the naphtha-comprising feedstock (1) and the catalyst (2) between 200 milliseconds and 20 seconds; and a partial pressure of hydrocarbons in the naphtha-comprising feedstock (1) between 0.02 and 0.3 MPa.

14. The process for producing olefins according to claim 1, wherein the aromatics extraction unit (30) comprises an olefin hydrogenation section for producing a low-olefin hydrogenation effluent comprising paraffins and aromatics; and an extraction section for separating the hydrogenation effluent and producing the aromatics-enriched fraction (31) and the low-aromatics fraction (32).

15. The process for producing olefins according to claim 1, which is performed on an apparatus for producing olefins having a number of carbon atoms of between 2 and 4 and aromatics by catalytic cracking, comprising the following units:
a naphtha catalytic cracking reactor (4) suitable for contacting some or all of a feedstock comprising naphtha (1), a catalyst (2) and a diluent (3), converting at least partly the naphtha-comprising feedstock (1) into olefins having a number of carbon atoms between 2 and 4, and producing a cracking effluent (6);
a first separating section (9) suitable for treating the cracking effluent (6) and producing at least the following fractions:
a fraction comprising ethylene (13),
a fraction comprising propylene (14), and
a fraction comprising compounds comprising at least 5 carbon atoms (16), comprising paraffins, olefins and aromatics;
a second separating section (24) suitable for treating at least part of the fraction comprising compounds comprising at least 5 carbon atoms (16), and producing the following fractions:
a fraction comprising compounds comprising 5 carbon atoms (25), and
a fraction comprising compounds comprising at least 6 carbon atoms (26) which is rich in aromatics;
an aromatics extraction unit (30) suitable for treating at least part of the fraction comprising compounds comprising at least 6 carbon atoms (26), and producing the following fractions:
an aromatics-enriched fraction (31), and
a low-aromatics fraction (32); and
an aromatics separation unit (33) suitable for treating at least part of the aromatics-enriched fraction (31), and producing at least the following fractions:

a benzene-rich fraction (34),
a toluene-rich fraction (35), and
at least one xylenes-rich fraction (36); and
a duct suitable for recycling at least partly the fraction comprising compounds comprising 5 carbon atoms (25) into the naphtha catalytic cracking reactor (4).

* * * * *